US008879070B2

(12) United States Patent
Yasuno et al.

(10) Patent No.: US 8,879,070 B2
(45) Date of Patent: Nov. 4, 2014

(54) TWO BEAMS FORMED BY WOLLASTON PRISM IN SAMPLE ARM IN AN OPTICAL COHERENCE TOMOGRAPHY APPARATUS

(75) Inventors: Yoshiaki Yasuno, Tsukuba (JP); Shuichi Makita, Tsukuba (JP); Masahide Ito, Tsukuba (JP)

(73) Assignee: University of Tsukuba, Tsukuba-Shi (JP)

( * ) Notice: Subject to any disclaimer, the term of this patent is extended or adjusted under 35 U.S.C. 154(b) by 388 days.

(21) Appl. No.: 13/375,427

(22) PCT Filed: Jun. 7, 2010

(86) PCT No.: PCT/JP2010/059603
§ 371 (c)(1),
(2), (4) Date: Jan. 5, 2012

(87) PCT Pub. No.: WO2010/143601
PCT Pub. Date: Dec. 16, 2010

(65) Prior Publication Data
US 2012/0120408 A1    May 17, 2012

(30) Foreign Application Priority Data

Jun. 11, 2009    (JP) .................................. 2009-140056

(51) Int. Cl.
*G01B 11/02*    (2006.01)
(Continued)

(52) U.S. Cl.
CPC ............ *G01N 21/4795* (2013.01); *A61B 3/102* (2013.01); *A61B 3/1233* (2013.01); *A61B 5/0066* (2013.01)
USPC .......................................... 356/495; 356/497

(58) Field of Classification Search
CPC .... G01B 9/0209; A61B 5/0062; A61B 3/102; A61B 3/10; A61B 3/12; G01N 21/17

USPC .................................. 356/479, 497, 490–495
See application file for complete search history.

(56) References Cited

U.S. PATENT DOCUMENTS 5,877,856 A    3/1999    Fercher
6,006,128 A    12/1999    Izatt et al.
(Continued)

FOREIGN PATENT DOCUMENTS

JP    H10-099337 A    4/1998
JP    H11-325849 A    11/1999
(Continued)

OTHER PUBLICATIONS

B. R. White, et al., Optics Express, vol. 11, No. 25 (2003), pp. 3490-3497.
(Continued)

*Primary Examiner* — Hwa Lee
(74) *Attorney, Agent, or Firm* — Law Office of Katsuhiro Arai

(57) ABSTRACT

The scanning speed of a sample in Doppler OCT, etc., is increased to enable quick measurement of blood flow rate, blood flow volume, etc. Wideband light from a light source 2 is linearly polarized by a polarization controller 3 and this linearly polarized beam is split into vertically polarized light and horizontally polarized light using a Wollaston prism 14 at a sample arm, which are then irradiated simultaneously onto two different locations of the sample in the scanning direction using a galvanometer mirror 18, and reference light from a reference arm 5 and object light from a sample arm 6 are merged and caused to interfere with each other, with the resulting interference signal light passed through a diffraction grating 26 for spectroscopy, while the horizontal component and vertical component are separated by a polarized beam splitter 28, to simultaneously measure the components with two polarization-sensitive optical detectors 29, 30 and thereby obtain two tomography images of the same location at different times by one mechanical scan, thus allowing the amount of temporal change in phase to be measured using the two tomography images.

1 Claim, 7 Drawing Sheets

(51) Int. Cl.
*G01N 21/47* (2006.01)
*A61B 3/10* (2006.01)
*A61B 3/12* (2006.01)
*A61B 5/00* (2006.01)

(56) References Cited

U.S. PATENT DOCUMENTS

| | | | |
|---|---|---|---|
| 6,377,349 B1 | 4/2002 | Fercher | |
| 6,549,801 B1 | 4/2003 | Chen et al. | |
| 6,665,456 B2 * | 12/2003 | Dave et al. | 385/11 |
| 7,710,577 B2 | 5/2010 | Yatagai et al. | |
| 8,352,022 B2 * | 1/2013 | Akkin et al. | 600/544 |
| 8,425,036 B2 * | 4/2013 | Yoshida et al. | 351/205 |
| 2008/0030740 A1 * | 2/2008 | Wang | 356/477 |
| 2008/0231807 A1 * | 9/2008 | Lacombe et al. | 351/215 |
| 2011/0096293 A1 * | 4/2011 | Hirose et al. | 351/206 |
| 2012/0327423 A1 * | 12/2012 | Hanebuchi | 356/497 |

FOREIGN PATENT DOCUMENTS

| | | |
|---|---|---|
| JP | 2002-310897 A | 10/2002 |
| JP | 2004-028970 A | 1/2004 |
| JP | 2007-298461 A | 11/2007 |
| JP | 4138027 B | 8/2008 |
| JP | 2009-165710 A | 7/2009 |

OTHER PUBLICATIONS

R. A. Leitgeb, et al., Optics Express, vol. 11, No. 23 (2003), pp. 3116-3121.

Yoshiaki Yasuno, "30 Seitai Fukukussetsu no Kashika—Henko Kanjugata Optical Coherence Tomography—", Optical and Electro-optical Engineering Contact, Aug. 20, 2007, vol. 45, No. 8, pp. 409 to 414.

* cited by examiner (a)

(b)

TWO BEAMS FORMED BY WOLLASTON PRISM IN SAMPLE ARM IN AN OPTICAL COHERENCE TOMOGRAPHY APPARATUS

This application is the U.S. National Phase under 35 U.S.C. §371 of International Application PCT/JP2010/059603, filed Jun. 7, 2010, which claims priority to Japanese Patent Application No. 2009-140056, filed Jun. 6, 2009. The International Application was published under PCT Article 21(2) in a language other than English.

TECHNICAL FIELD

The present invention relates to a two-beam optical coherence tomography apparatus, and specifically to a two-beam optical coherence tomography apparatus that can be applied for quantitative measurement apparatuses for eye fundus blood flow volume (blood flow volume in the blood vessels of the retina).

BACKGROUND ART

Traditionally "optical coherence tomography" (OCT) has been used to understand information of the inside of an object, or specifically the differential structure of refractive index distribution, in a nondestructive manner at high resolution.

OCT is a nondestructive tomography measurement technology used in the medical field, etc. (refer to Patent Literature 1). OCT uses light as probe beam (measurement light), which provides the advantage of being able to measure refractive index distribution, spectral information and polarization information (birefringence distribution) of a measuring target, among others.

A basic OCT 53 is based on Michelson's interferometer and its operating principle is explained using FIG. 7. Light emitted from a light source 44 is paralleled by a collimator lens 45, and then split into reference light and object light via a beam splitter 46. Object light is condensed into a measuring target 48 by an object lens 47 in the object arm, where it is scattered and reflected and then returned to the object lens 47 and beam splitter 46.

On the other hand, reference light passes through an object lens 49 in the reference arm, after which it is reflected by a reference mirror 50 and returned to the beam splitter 46 via the object lens 49. Thus returned to the beam splitter 46, this reference light enters a condensing lens 51, together with the object light, and both are condensed into an optical detector 52 (photodiode, etc.).

The light source 44 of the OCT utilizes light of temporally low coherence (light that makes it extremely unlikely for lights emitted from the light source at different timings to interfere with each other). With Michelson's interferometer, which uses temporally low coherence light as the light source, interference signals manifest only when the distance of the reference arm is roughly equivalent to the distance of the object arm. As a result, an interference signal relative to optical path length difference (interferogram) is obtained when the interference signal intensity is measured with the optical detector 52 by changing the optical path length difference ($\tau$) of the reference arm and object arm.

The shape of this interferogram represents the reflectance distribution of the measuring target 48 in the depth direction, where the structure of the measuring target 48 in the depth direction can be obtained by one-dimensional scanning in the axial direction. In other words, the OCT 53 can measure the structure of the measuring target 48 in the depth direction by means of optical path length scanning.

Two-dimensional scanning, comprising mechanical scanning in the lateral direction in addition to the above scanning in the axial direction, can obtain a two-dimensional section image of the measuring target. A scanning apparatus that performs the above scanning in the lateral direction may be structured to directly move the measuring target, structured to shift the object lens with the measuring target fixed, or structured to rotate the angle of the galvanometer mirror placed near the pupil surface of the object lens with the measuring target and object lens fixed, among others.

Advanced versions of the aforementioned basic OCT include swept source OCT ("SS-OCT") where the wavelength of the light source is scanned to obtain spectral interference signals, and spectral domain OCT ("SD-OCT") where a spectroscope is used to obtain spectral interference signal lights. Fourier domain OCT ("FD-OCT"; refer to Patent Literature 2) and polarization-sensitive OCT ("PS-OCT"; refer to patent Literature 3) are examples of the latter.

In SS-OCT, a high-speed wavelength scanning laser is used to change the wavelength of the light source, and the light-source scanning signals obtained synchronously with spectral signals are used to rearrange interference signals, to which signal processing is applied to obtain a three-dimensional optical tomography image. SS-OCT can also use a monochrometer as a means for changing the wavelength of the light source.

In FD-OCT, the wavelength spectrum of the reflected light from the measuring target is obtained with a spectrometer and the resulting spectral intensity distribution is Fourier-transformed to extract signals in the actual space (OCT signal space). This FD-OCT does not require scanning in the depth direction, and the section structure of the measuring target can be measured only by scanning in the x-axis direction.

PS-OCT is similar to FD-OCT in that the wavelength spectrum of the reflected light from the measuring target is obtained with a spectrometer, where the difference is that with PS-OCT, incident light and reference light are passed through a ½ wave plate and ¼ wave plate, etc., respectively, for horizontal linear polarization, vertical linear polarization, 45° linear polarization or circular polarization, and reflected light and reference light from the measuring target are superimposed and passed through a ½ wave plate, ¼ wave plate, etc., to cause only the horizontally polarized light component to enter the spectrometer to cause interference, for example, thereby extracting and Fourier-transforming only the component of object light having a specific polarization condition. This PS-OCT does not require scanning in the depth direction, either.

Furthermore, technologies using Doppler optical coherence tomography ("Doppler OCT"), such as technology to measure the blood flow distribution of retina, technology to form a transverse blood flood image of retina, and technology to three-dimensionally observe the capillary structure of retina, are known, among others. In Doppler OCT, the blood flow rate, etc., is obtained by utilizing the fact that the amount of temporal change in phase (change in frequency) obtained by Fourier transformation of spectral interference information corresponds to the moving speed of the target as the Doppler signal, where SS-OCT, FD-OCT, etc., can be applied (refer to Patent Literatures 4, 5 and Non-patent Literatures 1, 2).

The inventors named under the present application for patent have also proposed a quantitative measurement apparatus for eye fundus blood flow volume, whereby the structure of blood vessels of the retina is extracted by means of Doppler OCT angiography to allow for quantification of blood flow volume in the blood vessels of the retina (refer to Japanese Patent Application No. 2008-8465).

BACKGROUND ART LITERATURES

Patent Literatures

Patent Literature 1: Japanese Patent Laid-open No. 2002-310897
Patent Literature 2: Japanese Patent Laid-open No. Hei 11-325849
Patent Literature 3: Japanese Patent Laid-open No. 2004-028970
Patent Literature 4: U.S. Pat. No. 6,549,801
Patent Literature 5: Japanese Patent No. 4138027

Non-Patent Literatures

Non-patent Literature 1: B. R. White, et al., Optics Express, Vol. 11, No. 25 (2003), pp. 3490-3497
Non-patent Literature 2: R. A. Leitgeb, et al., Optics Express, Vol. 11, No. 23 (2003), pp. 3116-3121

SUMMARY OF THE INVENTION

Problems to be Solved by the Invention

Doppler OCT provides a means whereby, for example, a probe beam (measurement light) is irradiated twice onto a specified location of the sample at a time difference $\Delta t$ to measure the blood flow rate at this specified location of the sample, and the two resulting tomography images are used to obtain the amount of temporal change in phase $\Delta\emptyset$ (hereinafter simply referred to as "amount of change in phase" or "phase difference"), after which the amount of temporal change in frequency (hereinafter simply referred to as "frequency shift") is calculated from this amount of change in phase $\Delta\emptyset$ to calculate the blood flow rate at the applicable location using the optical Doppler effect.

Accordingly, measurement requires two irradiations of a probe beam onto the applicable location of the sample at an interval of at least $\Delta t$, which presents the problem of longer scanning time or longer time needed to obtain a tomography image. In effect, Doppler OCT has the problem of having to lower the scanning speed and take time to measure the same location multiple times in order to raise the sensitivity of the flow rate.

The object of the present invention is to resolve the problem inherent in conventional Doppler OCT, etc., which is having to irradiate a probe beam onto the same location of the sample multiple times and a resulting slowdown in the scanning speed because of this measurement, and to allow for quick measurement of blood flow rate, blood flow volume, etc., by applying Doppler OCT to a quantitative measurement apparatus for eye fundus blood flow volume.

Means for Solving the Problems

To achieve the aforementioned object, the present invention provides a two-beam optical coherence tomography apparatus comprising a wideband light source, a polarization controller, a fiber coupler, a reference arm, a sample arm and a spectrometer, wherein such two-beam optical coherence tomography apparatus is characterized in that:
light from the wideband light source is linearly polarized by the polarization controller; the linearly polarized beam is split into a vertically polarized beam and a horizontally polarized beam, or a clockwise circularly polarized beam and a counterclockwise circularly polarized beam, or other two mutually independent polarized beams at the sample arm; and the two polarized beams are simultaneously irradiated onto two different locations in the scanning direction using a galvanometer mirror to perform scanning; and reference light from the reference arm and object light from the sample arm are merged and caused to interfere with each other to produce interference signal light, which is then passed through a diffraction grating of the spectrometer for spectroscopy and further separated into a vertical component and a horizontal component using a polarized beam splitter; the respective components are simultaneously detected with two detectors to obtain two tomography images of the same location at different times by one mechanical scan as mentioned above; and the obtained two tomography images are used to measure the amount of temporal change in phase at the same location.

To achieve the aforementioned object, the present invention provides a two-beam optical coherence tomography apparatus comprising a wideband light source, a polarization controller, a fiber coupler, a reference arm, a sample arm and a spectrometer, wherein such two-beam optical coherence tomography apparatus is characterized in that:
the polarization controller linearly polarizes the beam from the wideband light source;
the sample arm comprises a Wollaston prism and a galvanometer mirror;
the Wollaston prism splits the linearly polarized light into a vertically polarized beam and a horizontally polarized beam, or a clockwise circularly polarized beam and a counterclockwise circularly polarized beam by placing a wave plate or other polarization conversion element after the Wollaston prism, or other two mutually independent polarized beams;
the galvanometer mirror performs scanning by simultaneously irradiating the two polarized beams onto two different locations of the sample in the scanning direction of the galvanometer mirror;
the spectrometer comprises a diffraction grating, a polarized beam splitter and two polarization-sensitive optical detectors;
the fiber coupler merges the reference light from the reference arm and object light from the sample arm and causes them to interfere with each other to produce interference signal light;
the diffraction grating converts the interference signal light into spectral interference signal light by means of spectroscopy;
the polarized beam splitter separates the spectral interference signal light into a vertically polarized component and a horizontally polarized component; and
the two optical detectors simultaneously detect the vertically polarized component and the horizontally polarized component of the spectral interference signal light to obtain two tomography images of the same location at different times by one mechanical scan as mentioned above, and the obtained two tomography images are used to measure the amount of temporal change in phase at the same location.

Desirably the constitution of the apparatus should be such that the blood vessel structure in the sample is extracted from the tomography image and the change in frequency calculated based on the amount of temporal change in phase is used to allow for calculation of the blood flow rate and blood flow volume in the aforementioned blood vessel structure.

Desirably the constitution of the apparatus should be such that it can be utilized as a quantitative measurement apparatus for eye fundus blood flow volume capable of quantifying the blood flow volume in the blood vessels of the retina by extracting the blood vessel structure of the retina as the aforementioned blood vessel structure.

Effects of the Invention

With a two-beam optical coherence tomography apparatus pertaining to the present invention, the same location of the sample can be measured at different times using two polarized beams shifted by a specified interval in the scanning direction, even when the scanning speed is increased, to obtain two tomography images reflecting different measurement timings, and these two tomography images can be used to obtain the amount of change in phase or frequency shift (change in frequency) between different times at the same location of the sample, thereby allowing for high-speed tomography image measurement of flow rate distribution at high sensitivity.

Also with normal Doppler OCT that measures the same location of the sample using one probe beam, an attempt to measure the same location of the sample twice with a minimum time difference using one probe beam with the aim of increasing the scanning speed would generate noise because the time difference is too short and consequently the Doppler frequency shift cannot be measured sufficiently. Under the present invention, on the other hand, data of two tomography images is used to calculate the amount of change in phase or frequency shift, and by increasing the time difference at which these two tomography images are obtained, the measurement sensitivity of Doppler frequency shift can be improved.

BRIEF DESCRIPTION OF THE DRAWINGS

The patent or application file contains at least one drawing executed in color. Copies of this patent or patent application publication with color drawing(s) will be provided by the Office upon request and payment of necessary fee.

MODE FOR CARRYING OUT THE INVENTION

The following explains a mode for carrying out a two-beam optical coherence tomography apparatus pertaining to the present invention based on an example with reference to the drawings.

Figure 1:
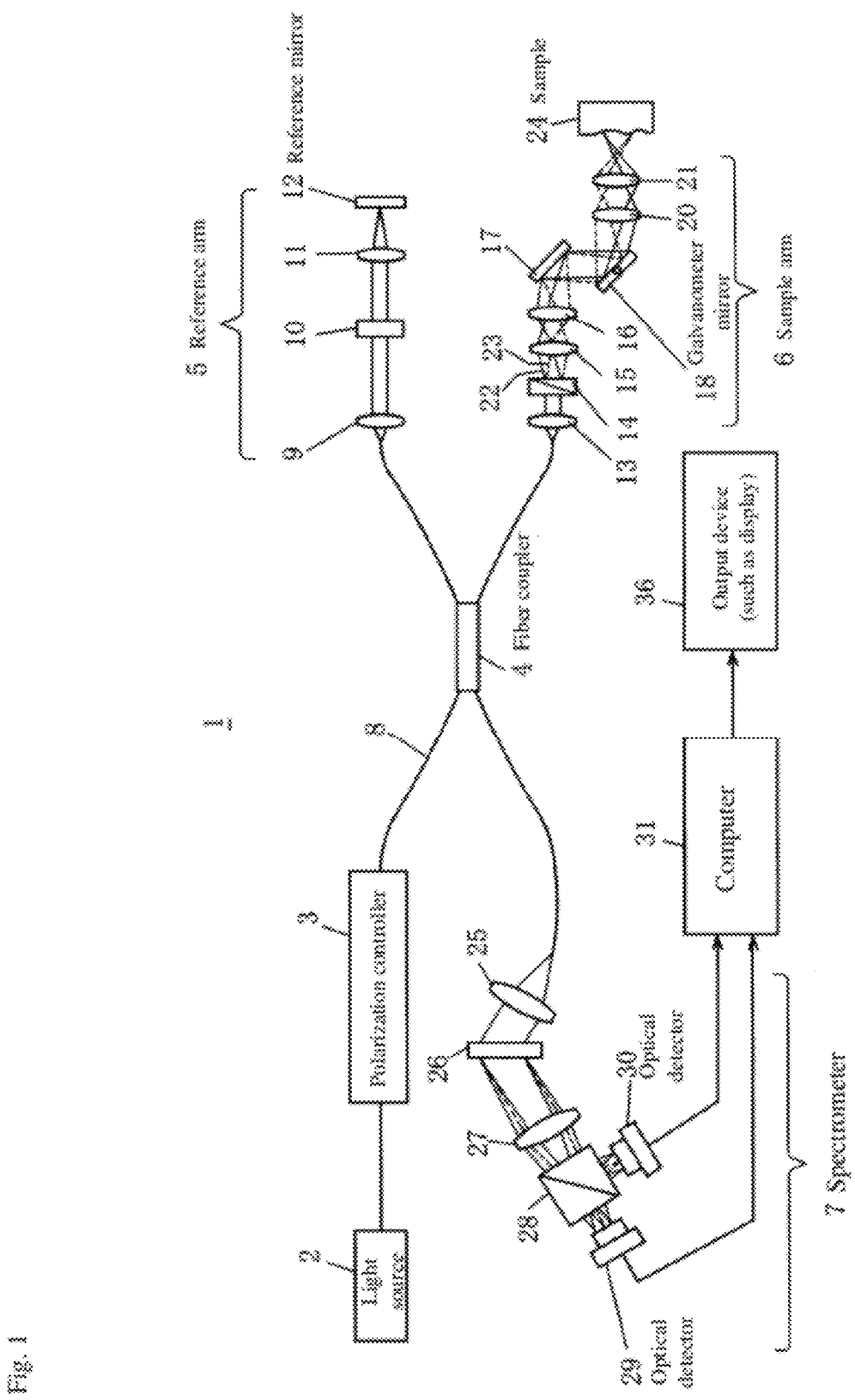
FIG. 1 Drawing explaining the overall constitution of a two-beam optical coherence tomography apparatus pertaining to the present invention.

First, the overall constitution of a two-beam optical coherence tomography apparatus pertaining to the present invention is explained using FIG. 1. This two-beam optical coherence tomography apparatus 1 has the basic constitution of spectral domain OCT (SD-OCT) where the principle of low coherence interference is used to obtain spectral interference signal light with a spectrometer and then obtain the resolution in the depth direction.

The two-beam optical coherence tomography apparatus 1 comprises a light source 2, a polarization controller 3, a fiber coupler 4, a reference arm 5, a sample arm 6 and a spectrometer 7, and these optical elements are connected via a fiber 8, as shown in FIG. 1. For the fiber 8, ideally polarization retention fibers should be used to maintain the polarization of light that has been linearly polarized by the polarization controller 3.

For the light source 2, a SLD (super luminescent diode), ultra-short pulse laser or other wideband light source is used. The polarization controller 3 is provided so that it linearly polarizes the light from the light source 2 and also adjusts the polarization direction (polarization angle) of linear polarization. The polarization controller 3 is connected to the fiber coupler 4.

The fiber coupler 4 is connected to the reference arm 5 and sample arm 6 via the two branching fibers 8. The reference arm 5 has a collimator lens 9, a light quantity adjustment unit 10 (a neutral density (ND) filter may be used for the light quantity adjustment unit), a condensing lens 11 and a reference mirror 12 (fixed mirror) in this order. The light quantity adjustment unit 10 is provided to prevent change in the intensity of the returning reference light after it has been reflected by the reference mirror 12. Note that, while the reference light linearly polarized by the polarization controller 3 is introduced to the reference arm 5 and then reflected by the reference mirror 12, this reference light contains both horizontal and vertical components.

The sample arm 6 has a collimator lens 13, a Wollaston prism (WP) 14, a condensing lens 15, a collimator lens 16, a fixed mirror 17, a galvanometer mirror 18, a collimator lens 20 and a condensing lens 21 in this order. The Wollaston prism, which is an example of a polarization separation element, is a polarization prism constituted by two prisms connected to each other, where light that enters vertically is separated by the two prisms into mutually orthogonal polarization conditions and emitted in different directions.

The polarized beam entering from the fiber coupler 4 is separated by the Wollaston prism 14 into the horizontally polarized component (horizontally polarized beam 22; refer to the solid line in FIG. 1) and the vertically polarized component (vertically polarized beam 23, refer to the dotted line in FIG. 1). The horizontally polarized beam 22 and vertically polarized beam 23 are further separated spatially at an appropriate interval δ in the below-mentioned scanning direction (direction B). This way, two probe beams of the horizontally polarized beam 22 and the vertically polarized beam 23 are formed at the interval δ in the scanning direction.

Note that, by inserting a wave plate or other polarization conversion element in the optical path after the Wollaston prism 14, the polarized beam entering from the fiber coupler 4 can be separated into a clockwise circularly polarized beam 22 and a counterclockwise circularly polarized beam 23 or other two mutually independent circularly polarized beams, instead of the horizontally polarized beam 22 and the vertically polarized beam 23, and emitted in different directions. These two circularly polarized beams of different rotating directions can also be used. These two circularly polarized beams separated by the Wollaston prism 14 and wave plate are also spatially separated at an appropriate interval δ in the below-mentioned scanning direction (direction B), just like the horizontally polarized beam 22 and the vertically polarized beam 23.

Then, the horizontally polarized beam 22 and the vertically polarized beam 23 that have been mutually separated in the scanning direction are oriented via the galvanometer mirror 18 to direction B, which is vertical to direction A being the depth direction of the sample 24, and simultaneously irradiated onto two different locations of a sample 24 in the scanning direction. This scanning method is the same when the clockwise circularly polarized beam 22 and the counterclockwise circularly polarized beam 23, etc., are used instead of the horizontally polarized beam 22 and the vertically polarized beam 23.

The backscattering light (reflected light) from the sample 24 corresponding to the irradiated horizontally polarized beam 22 and that corresponding to the vertically polarized beam 23 travel through the Wollaston prism 14 and return to the fiber coupler 4 as object light containing horizontal and vertical components, after which it is superimposed and merged with reference light to cause interference and the resulting interference signal light containing two vertically and horizontally polarized components is sent to the spectrometer 7. Even when the clockwise circularly polarized beam 22 and the counterclockwise circularly polarized beam 23, etc., are used instead of the horizontally polarized beam 22 and the vertically polarized beam 23, interference signal light containing two vertically and horizontally polarized components is still sent to the spectrometer 7 just as above.

The spectrometer 7 has, along the optical path, a collimator lens 25, a diffraction grating 26, a Fourier transformation lens 27, a polarized beam splitter 28 and two optical detectors 29, 30, in this order. The polarized beam splitter 28 and two optical detectors 29, 30 constitute a polarization-sensitive detection unit.

The interference signal light sent from the fiber coupler 4 enters the diffraction grating 26 via the collimator lens 25 and is converted, by means of spectroscopy, to spectral interference signal light containing two polarized components, or a vertically polarized component and a horizontally polarized component.

The spectral interference signal light containing two polarized components, produced by spectroscopy through the diffraction grating 26, is Fourier-transformed by the Fourier transformation lens 27 and the two polarized components are further separated via the polarized beam splitter 28 into spectral interference signal lights containing respective polarized components and simultaneously detected by the two polarization-sensitive optical detectors 29, 30, respectively, to allow two sets of OCT tomography image data (OCT signals) to be obtained simultaneously. For the two optical detectors 29, 30, line CCD cameras (one-dimensional CCD cameras), etc., are used.

Thus detected by the two optical detectors 29, 30, the two OCT signals are imported into a computer 31, where two OCT tomography images of the sample 24 are simultaneously formed with one scan, based on these two OCT signals. These two tomography images have tomography image information of the same sample 24 taken at different times as well as phase information contained in this tomography image information.

It should be noted that the optical Doppler effect is such that the frequency shift (change in frequency) of reflected light being irradiated onto a moving object corresponds to the speed of the object. Accordingly, the two-beam optical coherence tomography apparatus pertaining to the present invention allows for calculation of frequency shift between different times at the same location of the sample 24 based on extracted data of phase information at different times as contained in the specified same location of two tomography images obtained as above.

Based on this frequency shift, the blood flow rate in a specified location (such as a part of a blood vessel) can be measured, or even the blood flow volume, etc., can be measured based on the blood flow rate and the cross-section area of the blood vessel obtainable from the tomography image.

The principle and operation of a two-beam optical coherence tomography apparatus pertaining to the present invention is explained more specifically in greater detail below using mathematical formulas. The two-beam optical coherence tomography apparatus pertaining to the present invention is characterized by its constitution where two probe beams are used to increase the phase detection (flow rate) sensitivity without lowering the scanning speed.

Figure 2:
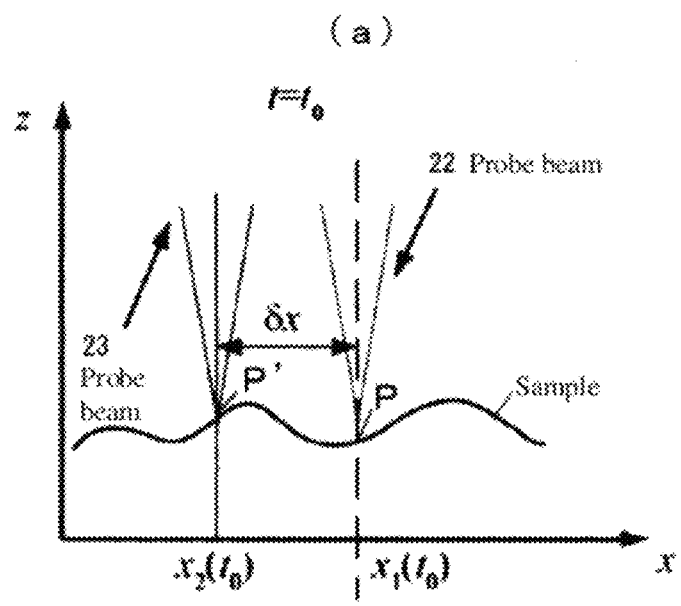
FIG. 2 Drawing explaining the principle and operation of the present invention.
Figure 2:
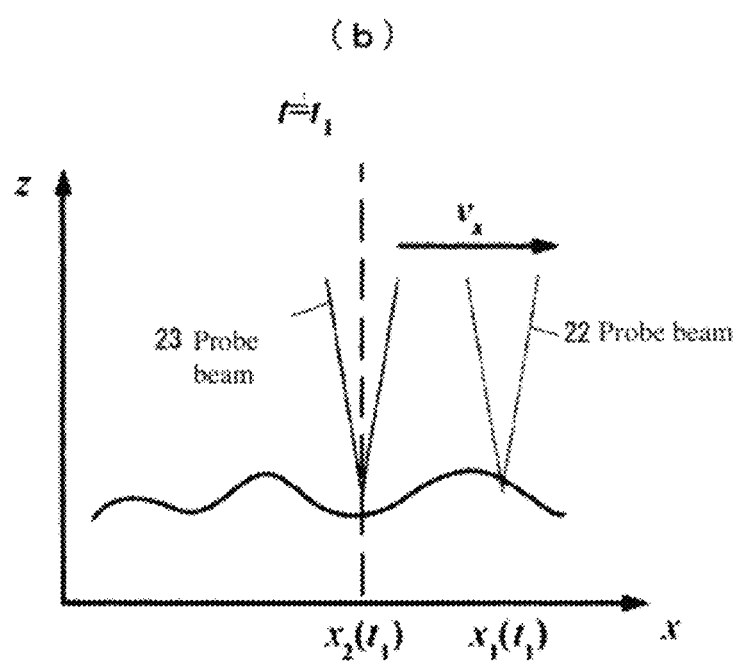

FIGS. 2(a) and (b) explain the conditions of the two-beam optical coherence tomography apparatus shown in FIG. 1, where the sample 24 is scanned using two probe beams 22, 23 (the horizontally polarized beam 22, the vertically polarized beam 23) that are spaced by δx representing the distance between the foci in the scanning direction (scanning direction B) and the same location P of the sample is irradiated at different times $t=t_0$, $t=t_1$. Here, x represents a position in the scanning direction (scanning direction B), while z represents a position in the depth direction of the sample 24 (scanning direction A). These point definitions are the same even when clockwise circularly polarized beam 22 and counterclockwise circularly polarized beam 23, etc., are used instead of the horizontally polarized beam 22 and the vertically polarized beam 23.

As shown in FIG. 2(a), at $t=t_0$, the probe beam 22 is condensed to $x_1(t_0)$ relative to the location P of the sample, while the probe beam 23 is condensed to $x_2(t_0)$ relative to the location P' of the sample. These two probe beams 22, 23 are simultaneously scanned at the speed of vx [mm/s].

Also as shown in FIG. 2(b), the probe beam 23 reaches $x_2(t_1)$ at $t=t_1$ relative to the location P of the sample. The position $x_1(t_0)$ in the scanning direction where the probe beam 22 is condensed at the time $t_0$ is the same as the position $x_2(t_1)$ in the scanning direction where the probe beam 23 is condensed at the time $t_1$.

In FIGS. 2(a) and (b), the OCT signal obtained by the probe beam 22 at $x_1(t_0)$ is the same as the OCT signal obtained by the probe beam 23 at $x_2(t_1)$ if there is no blood flow or any other movement at the specified location P of the sample 24, and consequently there is no amount of change in phase or frequency shift at the location P of the sample 24 between the times $t_0$ and $t_1$. If there is blood flow or other movement at the specified location P of the sample 24, on the other hand, there is an amount of change in phase or frequency shift at the location P of the sample 24 between the times $t_0$ and $t_1$.

Figure 3:
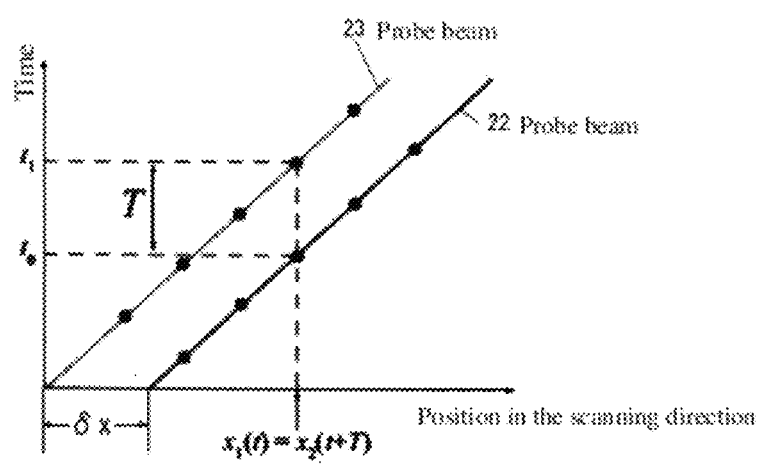
FIG. 3 Drawing explaining the principle and operation of the present invention.

FIG. 3 shows the position relationship and detection timings of two probe beams 22, 23. If the detection time difference of two beams $t_1-t_0$ is given as T in FIG. 3, then the position $x_1(t)$ where the probe beam 22 is condensed at the time t is the same as the position $x_2(t+T)$ where the probe beam 23 is condensed at the time t+T (refer to FIG. 3). Also, $T=\delta x/vx$. Here, δx represents the distance between two beams, while vx represents the scanning speed.

If there is blood flow or other movement at the specified location P of the sample 24, the amount of change in phase between the OCT signal $\Gamma_1(x_1(t), z_i)$ obtained by the probe beam 22 at $x_1(t)$ and the OCT signal $\Gamma_2(x_2(t+T), z_k)$ obtained by the probe beam 23 at $x_2(t+T)$ is expressed by Formula 1 below as the frequency shift.

$$\Delta f(x_1(t), z_i) = \frac{1}{2\pi T} \mathrm{Arg}\left[\sum_{k=i}^{i+M} \Gamma_1(x_1(t), z_k) * \Gamma_2(x_2(t+T), z_k)\right] \quad \text{[Formula 1]}$$

In Formula 1, x represents a position in scanning direction B, while z represents a position in scanning direction A. Also in Formula 1, * represents a complex conjugate. The meaning of Formula 1 is as follows. To reduce noise, OCT signals are added in the depth direction. The frequency shift at the i-th position zi in the depth direction, or $\Delta f(x_1(t), zi)$ is calculated as the sum of signals from the i-th signal $\Gamma_1$ ($x_1(t)$, $z_i$), $\Gamma_2$ ($x_2(t)$, $z_i$) through i+M-th signal $\Gamma_1$ ($x_1(t)$, $z_i$+M), $\Gamma_2$ ($x_2(t)$, $z_i$+M) in the depth direction. k is a z-direction parameter that changes from i to i+M.

This frequency shift $\Delta f(x_1(t), zi)$ expressed by Formula 1 represents the Doppler shift of the OCT signal due to the blood flow or other speed of movement (motion) in the direction of the optical axis at the specified location P of the sample 24. From the frequency shift (Doppler shift) $\Delta f$, the flow rate (blood flow rate) component $v_c$ in the direction of the optical axis (z-axis direction) is obtained by $v_c = \Delta f \lambda / 2n$. Here, $\lambda$ represents the center wavelength of the light source used for measurement, while n represents the refractive index of the measuring target. Since the actual blood vessel has an optical axis and angle $\theta$, the actual blood flow rate v is expressed by $v = v_c / \sin \theta$. For the direction of blood vessel $\theta$, anatomically known information may be used. Also because the diameter and other cross-section shape dimensions of the blood vessel can be quantified from the OCT intensity image, if the blood vessel is assumed to have a circular cross-section, its radius r can be used to estimate the flow volume (blood flow volume) per unit time V by $V = v \pi r^2$. This way, the blood flow rate at the specified location (such as a part of a blood vessel), or even blood flow volume, etc., can be calculated based on the obtained frequency shift. Also because the phase shift represents a small amount of deformation of biological tissue, this principle can also be applied to measurement of tissue motion.

As explained in the above description of principle and operation, the blood flow rate at the specified location P (such as a part of a blood vessel), and blood flow volume, etc., based on this rate, can be obtained, among other processing, based on the extracted phase data contained in the specified same location of two tomography images obtained simultaneously relative to two spectral interference signal lights of different polarized conditions.

To be specific, such processing takes the form of quantification of blood flow rate by a quantification means provided by the computer to which OCT signals are input (specifically functional means provided by quantification software). Furthermore, the diameter of the interior cavity of the blood vessel (or cross-section of the blood vessel), obtained based on the two OCT signals, is used to quantitatively measure the blood flow volume.

Figure 4:
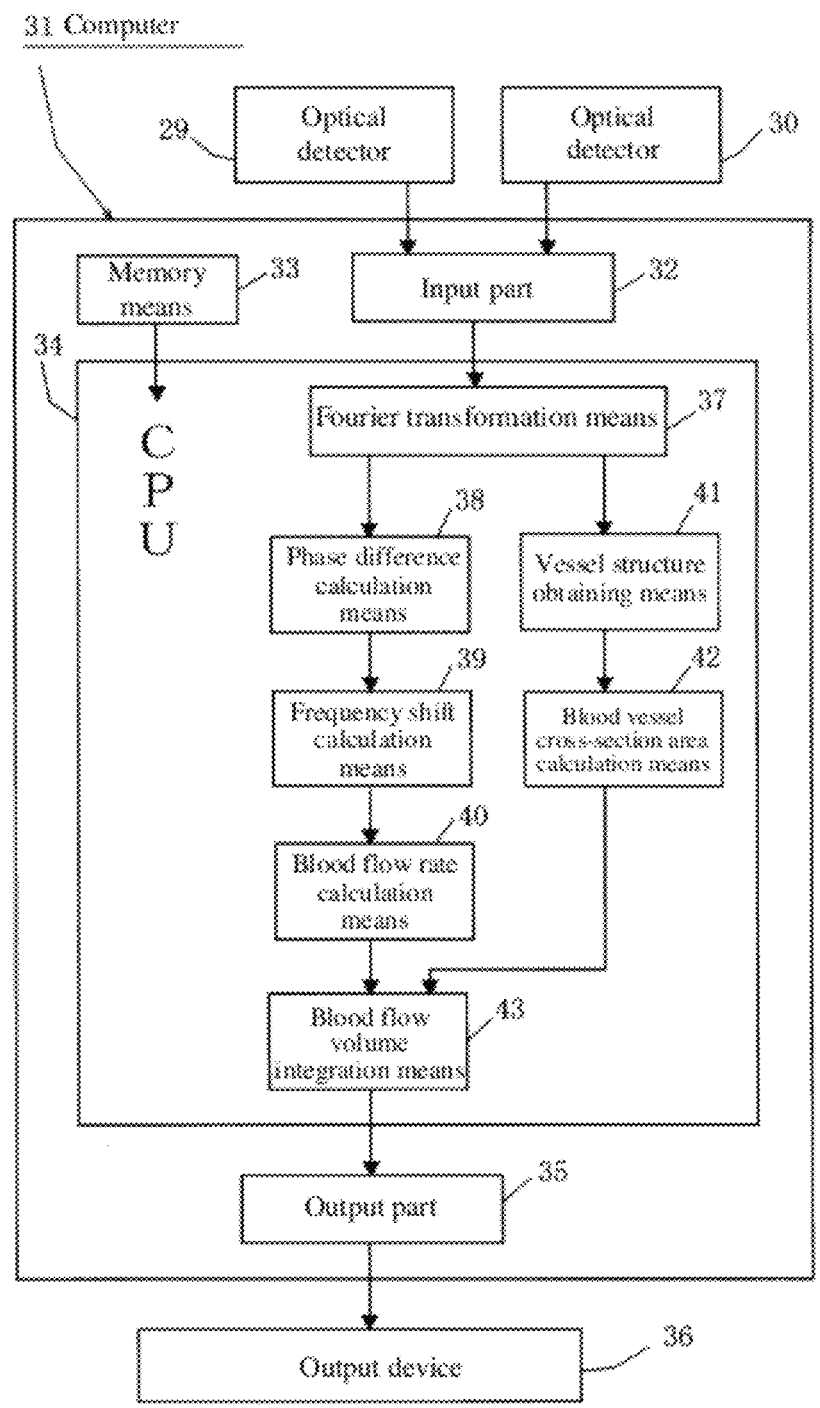
FIG. 4 Drawing explaining a means for computer-processing the tomography image data taken by a two-beam optical coherence tomography apparatus pertaining to the present invention.

FIG. 4 shows an example of a configuration of a computer that performs processing to obtain the blood flow rate at the specified location (such as a part of a blood vessel), blood flow volume, etc., based on the aforementioned two spectral interference signal lights of different polarized conditions. This computer 31 is a standard computer having an input part 32, a memory means 33, a CPU 34 and an output part 35, where signals output from the output part 35 are visualized by an output device 36 such as a display or printer. The CPU 34 executes a series of functions based on the quantification software installed in the memory means 33. Quantitative measurement of blood flow volume is explained below primarily with respect to the functions of quantification software.

The two tomography image signals obtained by the spectrometer 7 are input to the input part 32 of the computer 31 from the two optical detectors 29, 30 (such as CCD cameras), respectively. The spectral interference signal input to the input part 32 is Fourier-transformed by a Fourier transformation means 37, and the resulting complex number data is used to calculate the phase component by a phase difference calculation means 38. The amount of frequency shift calculated by a frequency shift calculation means 39 based on the phase component is converted to blood flow rate as the Doppler signal by a blood flow rate calculation means 40.

In the meantime, the blood vessel structure is extracted by a blood vessel structure obtaining means 41 based on the intensity component of the Fourier-transformed spectral interference signal (normal OCT image), and the result is used to calculate the cross-section area of the blood vessel by a blood vessel cross-section area calculation means 42. The blood flow volume is calculated by a blood flow volume integration means 43 from the blood flow rate and cross-section area of the blood vessel, and the three-dimensional structure and blood flow volume in the blood vessel are displayed on the display (output device).

EXAMPLES

A measurement experiment was conducted using the two-beam optical coherence tomography apparatus shown in FIG. 1, where the sample 24 was a human retina. Using a super-luminescent diode (SLD) as the wideband light source, the polarization direction of wideband light from the light source was controlled by the polarization controller 3 to implement conversion in such a way that the horizontal component and the vertical component of linear polarization became 1:1, and the converted light was introduced to the fiber coupler 4 via the optical fibers 8. Then, the linearly polarized light was caused to enter the reference arm 5 and sample arm 6 from the fiber coupler 4.

The backscattering light from the sample arm 6 and reference light from the reference arm 5 were merged by the fiber coupler 4 to cause interference, which was followed by spectroscopy at the diffraction grating 26 and the resulting light was then separated into the horizontally polarized component and the vertically polarized component using the polarized beam splitter 28, to allow for simultaneous detection of both components using one-dimensional CCD cameras.

Light from the wideband light source used in this example may have a center frequency of 840 nm and a spectral width of 50 nm, for example. The Wollaston prism 14 separates the horizontally polarized component and the vertically polarized component by 0.35 degree. The separation interval $\delta x$ between the two probe beams 22, 23 on the sample 24 is 162 microns.

Figure 5:
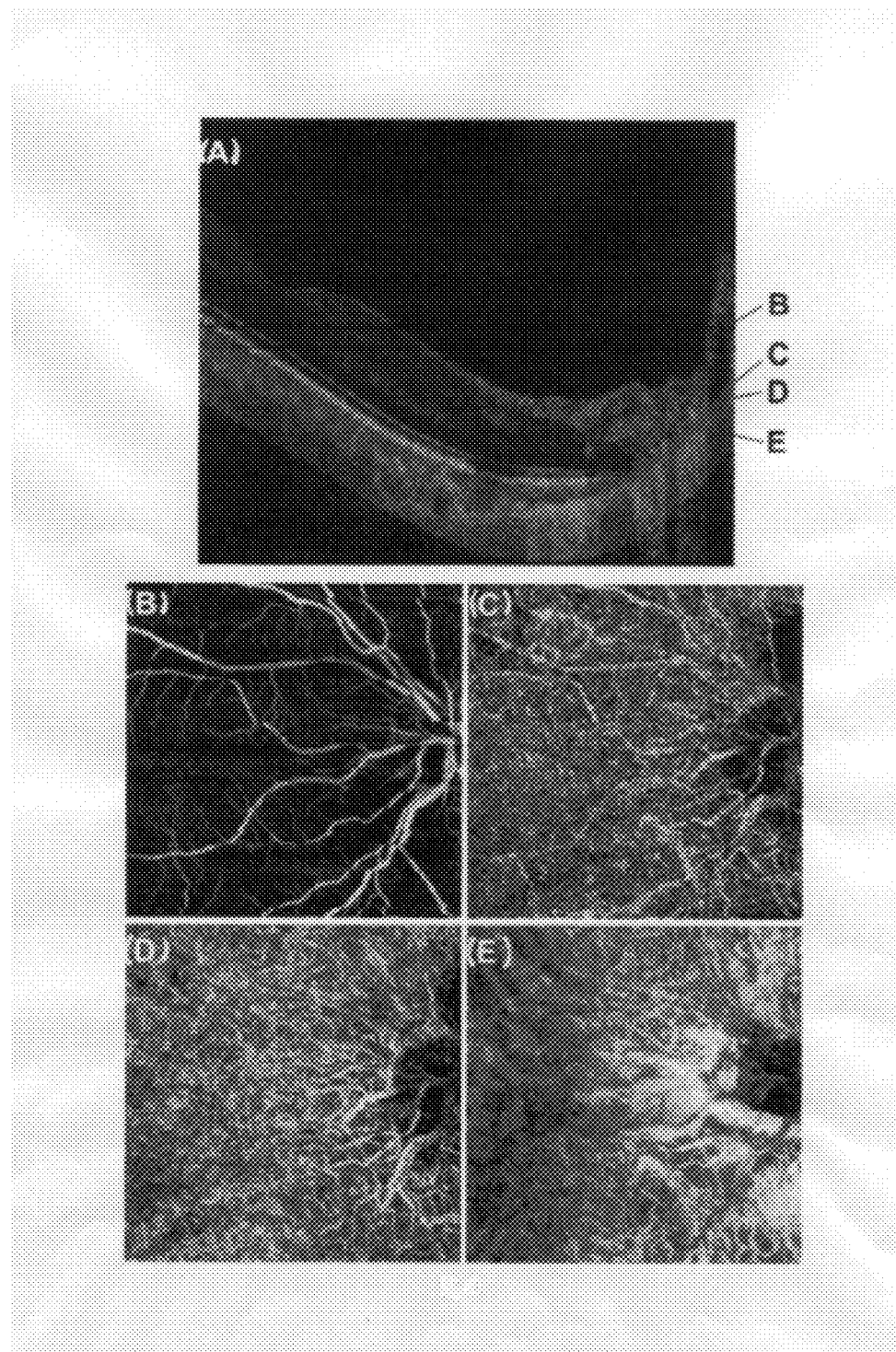
FIG. 5 Drawing explaining the result of carrying out an example of the present invention.
Figure 6:
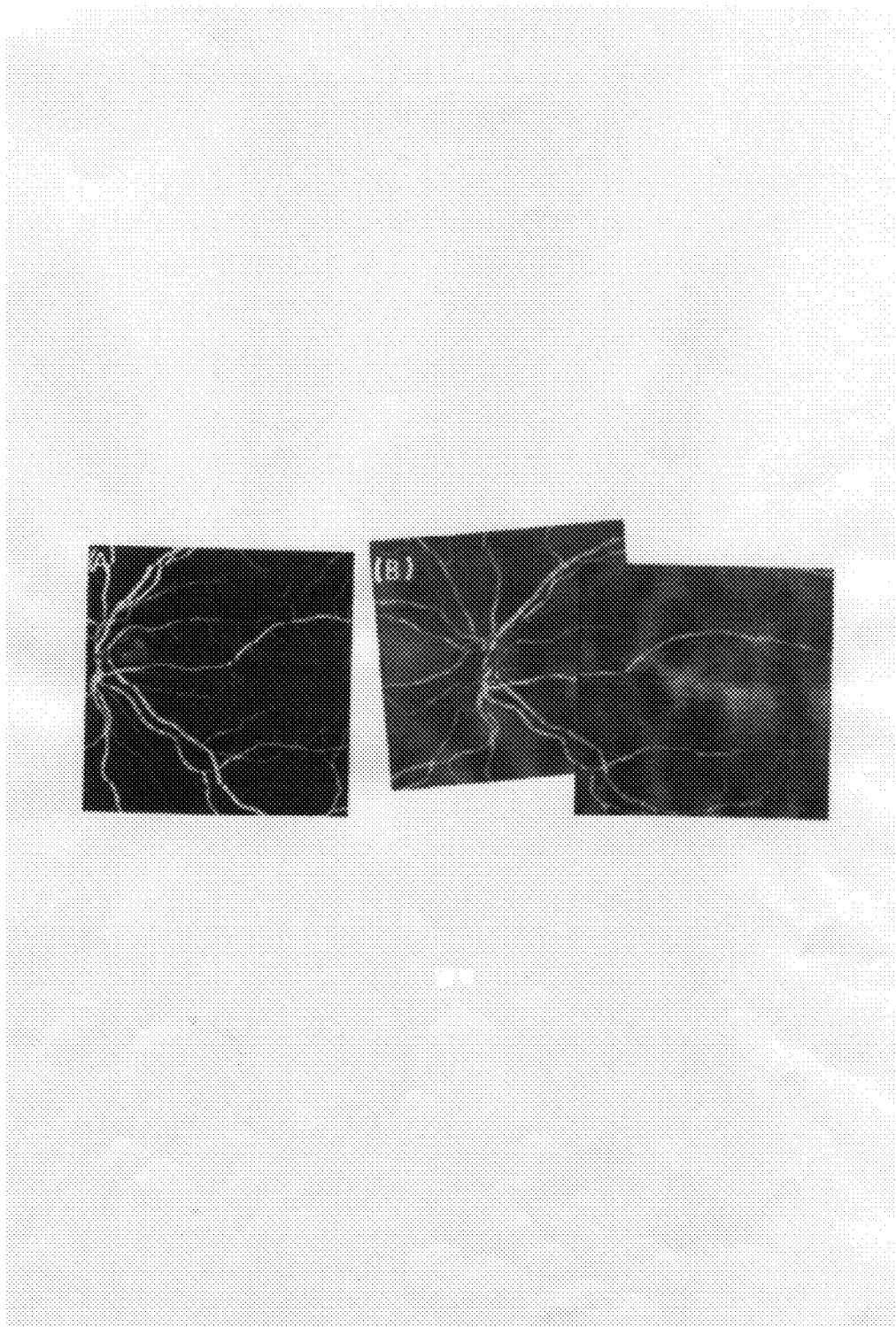
FIG. 6 Drawing explaining the result of carrying out an example of the present invention.
Figure 7:
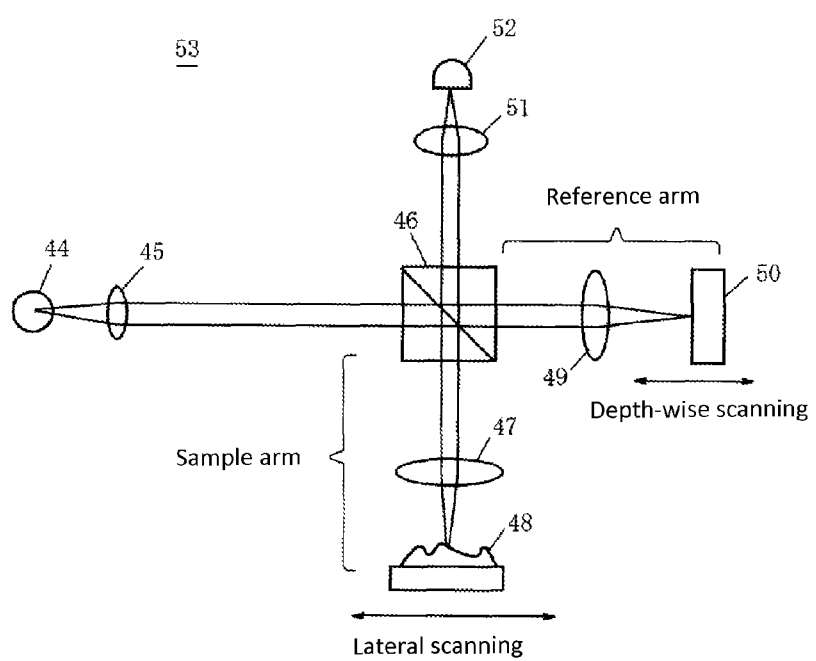
FIG. 7 Drawing explaining a conventional basic OCT.

In this example, the scanning range was 7.7×7.7 mm and the measurement time was 5 seconds. FIG. 5(A) shows an OCT image of a human retina. FIGS. 5(B), (C), (D) and (E) show OCT Doppler images at depths B, C, D and E, respectively. FIG. 6(A) is an OCT Doppler image obtained from this example, while FIG. 6(B) is an OCT Doppler image obtained by conventional OCT. Clearly, the sensitivity (definition) is better with the former.

Note that the term "OCT Doppler image" represents something different from a normal OCT image (tomography image) in the following sense. Normally an OCT image (or tomography image which is the same thing) shows intensity (intensity distribution) of an OCT signal (Fourier transformation of spectral interference signals detected by a CCD camera following spectroscopy by a spectrometer). The Fourier transformation result of an OCT signal provides a complex number, and the OCT image shows the absolute value of this complex number.

Note that the phase component of complex number becomes constant if the phase of the measuring target does not change temporally (the target does not move). If there is blood flow or other temporal movement at a given location of the sample, the phase varies at different measurement times even though the intensity component (reflectance) is the same. The OCT Doppler image shows these varying phases that have been converted to a frequency shift (Doppler signals) (converted to pixel brightness for clear identification).

As explained above, the two-beam coherence tomography apparatus pertaining to the present invention scans (B scan) the same point (same location of the sample) at different times via probe beams 22, 23, meaning that the OCT signal obtained by the probe beam 22 is shifted by the time T from the OCT signal obtained by the probe beam 23.

Then, the amount of change between the phase components of these two OCT signals is used to obtain an OCT Doppler image. Normally B scan and C scan must be repeated twice to obtain OCT signals at different times, but the two-beam coherence tomography apparatus pertaining to the present invention obtains OCT signals shifted by the time T with only one B scan and C scan using two probe beams.

When OCT signals are obtained at two times, it is believed that conventional Doppler OCT causes the image to be disturbed due to vibration, etc., during a full scan, etc., because the times are too far apart. If the times are too far apart, the phase relationship is also disrupted.

On the other hand, the two-beam coherence tomography apparatus pertaining to the present invention allows an OCT Doppler image to be created from images taken at adjacent times, which minimizes to relatively low levels the problems, under the conventional Doppler OCT, of image disturbance due to vibration and disruption of phase relationship due to the measurement times being too far apart, and consequently a clearer OCT Doppler image can be expected.

The above explains the best mode for carrying out the two-beam coherence tomography apparatus pertaining to the present invention based on an example. Note, however, that the present invention is not at all limited to this example and, needless to say, various examples may be considered within the scope of technical items stated in "Claims."

INDUSTRIAL FIELD OF APPLICATION

Having the aforementioned constitution, the two-beam coherence tomography apparatus pertaining to the present invention can be applied not only for quantitative measurement of eye fundus blood flow volume, but also for medical inspection devices as well as various technical fields where high resolution accuracy is required, such as vital observation and structural observation of animals and plants.

DESCRIPTION OF THE SYMBOLS

1 Two-beam coherence tomography apparatus
2 Light source
3 Polarization controller
4 Fiber coupler
5 Reference arm
6 Sample arm
7 Spectrometer
8 Fiber
9 Collimator lens
10 Light quantity adjustment unit
11 Condensing lens
12 Reference mirror
13 Collimator lens
14 Wollaston prism
15 Condensing lens
16 Collimator lens
17 Fixed mirror
18 Galvanometer mirror
20 Collimator lens
21 Condensing lens
22 Horizontally polarized beam, clockwise circularly polarized beam (probe beam)
23 Vertically polarized beam, counterclockwise circularly polarized beam (probe beam)
24 Sample
25 Collimator lens
26 Diffraction grating
27 Fourier transformation lens
28 Polarized beam splitter
29, 30 Optical detector
31 Computer
32 Input part
33 Memory means
34 CPU
35 Output part
36 Output device (such as display)
37 Fourier transformation means
38 Phase difference calculation means
39 Frequency shift calculation means
40 Blood flow rate calculation means
41 Vessel structure obtaining means
42 Blood vessel cross-section area calculation means
43 Blood flow volume integration means

The invention claimed is:

1. A two-beam optical coherence tomography apparatus, comprising:
    a wideband light source;
    a polarization controller which linearly polarizes the beam from the wideband light source;
    a sample arm which comprises:
        a Wollaston prism which splits the linearly polarized light into a vertically polarized beam and a horizontally polarized beam, or a clockwise circularly polarized beam and a counterclockwise circularly polarized beam by placing a polarization conversion element after the Wollaston prism; and
        a galvanometer mirror which performs scanning by simultaneously irradiating the vertically polarized beam and the horizontally polarized beam, or the clockwise circularly polarized beam and the counterclockwise circularly polarized beam, onto two different locations of a target sample in the scanning direction of the galvanometer mirror;
    a reference arm;
    a fiber coupler which merges reference light from the reference arm and object light from the sample arm and causes them to interfere with each other to produce interference signal light; and
    a spectrometer comprising:
        a diffraction grating which converts the interference signal light into spectral interference signal light by means of spectroscopy;

a polarized beam splitter which separates the spectral interference signal light into a vertically polarized component and a horizontally polarized component; and two optical detectors which simultaneously detect the vertically polarized component and the horizontally polarized component of the spectral interference signal light to obtain two tomography images of the same location at different times by one mechanical scan as mentioned above, and the obtained two tomography images are used to measure the amount of temporal change in phase at the same location.

* * * * *